United States Patent

Finch et al.

Patent Number: 6,132,415
Date of Patent: Oct. 17, 2000

[54] SYSTEMS AND METHODS FOR REMOVING RETAINED FLUIDS AND INFUSING THERAPEUTIC FLUIDS

[75] Inventors: Charles David Finch, Clinton, Miss.;
Jeffrey H. Burbank, Topsfield, Mass.;
James M. Brugger, Newport, Mass.;
John E. Moran, Beverly Farms, Mass.;
John H. Wang, North Andover, Mass.;
Hendrick K. Kuiper, Edwards, Miss.

[73] Assignee: Vasca, Inc., Tewksbury, Mass.

[21] Appl. No.: 09/248,156

[22] Filed: Feb. 9, 1999

[51] Int. Cl.⁷ .................................................. A61M 31/00
[52] U.S. Cl. ........................ 604/502; 604/93; 604/288.01
[58] Field of Search ................................. 604/502, 506, 604/93, 175, 176, 164, 30, 246, 28

[56] References Cited

U.S. PATENT DOCUMENTS

| | | | |
|---|---|---|---|
| 4,086,925 | 5/1978 | Dodge | 128/272 |
| 4,368,737 | 1/1983 | Ash | 604/175 |
| 4,560,378 | 12/1985 | Weiland | 604/83 |
| 4,753,636 | 6/1988 | Free | 604/49 |
| 4,802,885 | 2/1989 | Weeks et al. | 604/93 |
| 4,850,955 | 7/1989 | Newkirk | 604/9 |
| 4,886,501 | 12/1989 | Johnston et al. | 604/175 |
| 4,921,488 | 5/1990 | Maitz et al. | 604/153 |
| 5,078,689 | 1/1992 | Keller | 604/167 |
| 5,090,954 | 2/1992 | Geary | 604/29 |
| 5,092,849 | 3/1992 | Sampson | 604/175 |
| 5,215,530 | 6/1993 | Hogan | 604/174 |
| 5,542,923 | 8/1996 | Ensimnger et al. | 604/93 |
| 5,766,249 | 6/1998 | Griffith | 623/12 |
| 6,013,051 | 1/2000 | Nelson | 604/93 |

FOREIGN PATENT DOCUMENTS

WO 98/31416  7/1998  WIPO .......................... A61M 39/00

*Primary Examiner*—John D. Yasko
*Assistant Examiner*—Deborah Blyveis
*Attorney, Agent, or Firm*—Townsend and Townsend and Crew LLP

[57] ABSTRACT

Systems for draining retained body fluids comprise an implantable port in an access tube. Usually, a drainage cannula for connecting the implantable port to a site of fluid retention is also provided. The implantable port and drainage cannula are implanted subcutaneously with one end of the cannula within the site of fluid retention and the port located remotely from such site. Drainage may then be effected by percutaneously introducing the access tube to the port and optionally applying a vacuum. Kits comprise the implantable port together with instructions for implanting the port as described above. Kits also comprise an access tube with instructions for use for accessing an implanted port as described above.

10 Claims, 9 Drawing Sheets

SYSTEMS AND METHODS FOR REMOVING RETAINED FLUIDS AND INFUSING THERAPEUTIC FLUIDS

BACKGROUND OF THE INVENTION

1. Field of Invention

The present invention relates generally to medical apparatus and methods. More particularly, the present invention relates to systems, kits, and methods for removing endogenous fluids from or infusing therapeutic fluids to, retention sites in the body, such as the bladder, the pleural cavity, and the like.

Body fluids collect at different body sites for a variety of normal and abnormal reasons. For example, urine collects in the bladder as the result of normal body processes and, for most people at least, is removed from the bladder by periodic urination. In some individuals, urination may be difficult or impossible because of blockage of the urethra or other incapacities. In patients suffering from severe urinary incontinence, the urethra may be intentionally occluded in order to prevent uncontrolled urination but also preventing periodic urination needed to drain the bladder. Likewise, urine can accumulate in the upper urinary tract from ureteral obstructions requiring drainage. In all cases wherein the individual is unable to urinate at will, it may be necessary to provide interventional devices for permitting bladder drainage. Of particular interest to the present invention, such individuals are sometimes provided with transcutaneous catheters or shunts which permit drainage of the bladder to an external collection bag.

Another quite different condition which may require transcutaneous drainage results from the collection of effusate in the pleural cavity. Such pleural effusion can result from a variety of primary conditions, such as infection (empyema), cancer, asbestosis, congestive heart failure, and a number of other disorders. Chronic pleural effusion, particularly in cancer patients, can be treated by placement of a transcutaneous catheter having a collection end in the pleural cavity and a discharge end external to the patient.

The use of transcutaneous catheters for the drainage of the bladder, the pleural cavity, or other body sites is problematic in a number of respects. In particular, the presence of a transcutaneous catheter places the patient at great risk of infection because of the long-term percutaneous penetration that is maintained in the patient's skin. The presence of the external end of the catheter is difficult to maintain in a sterile condition, and it's physical presence is a great inconvenience to the patient.

Another condition which may require percutaneous drainage is the accumulation of ascites which result from liver, kidney, or heart disease or from obstruction of the inferior vena cava, hepatic vein, or portal vein. Ascites fluid accumulation can be considerable, causing discomfort or compromising breathing.

Another condition which can be treated with percutaneous drainage is hydrocephalus where cerebrospinal fluid (CSF) accumulates in the brain due to obstruction of flow or decreased reabsorption of CSF within the fluid filled structures of the central nervous system. Such accumulation increases ventricular pressure within and/or around the brain. Unless such excess CSF is removed, brain damage will occur.

Another condition that can be treated by percutaneous drainage is lymphodema which is an abnormal collection of lymph fluid within a tissue space or wound.

In addition to draining fluids, it is sometimes desirable to infuse fluids on a periodic or chronic basis to different body sites, often the same sites where fluids are being removed. For example, antibiotics can be administered to treat infections in the bladder, the pleural cavity, or other body cavities having transcutaneous catheters in place. Other therapeutic agents could also be administered, such as dissolving agents to treat stones in the bladder and kidney.

For these reasons, it would be desirable to provide alternative and improved apparatus, methods, and kits for providing drainage and/or infusion of retained fluids from body sites, such as the bladder, the pleural space, the liver, the kidney, the heart, the brain ventricles, the lymph spaces, and the like. Such apparatus, kits, and methods should reduce the risk of infection to the patient, be generally more tolerable to the patient than present drainage techniques, and preferably increase the safety and reliability of body fluid drainage. At least some of these objectives will be met by the invention described hereinafter.

2. Description of the Background Art

A transcutaneous tube for bladder drainage is described in U.S. Pat. No. 5,766,249. A transcutaneous system for draining the pleural cavity is described in U.S. Pat. No. 4,086,925. Transcutaneous catheters for peritoneal dialysis and other purposes are described in U.S. Pat. Nos. 5,215,530; 4,560,378; and 4,368,737. A percutaneous peritoneal dialysis system is described in U.S. Pat. No. 5,090,954. An internal shunt for draining pleural effusions to the peritoneal cavity is described in U.S. Pat. No. 4,850,955. An aspirator for draining the lungs of an infant is described in U.S. Pat. No. 4,921,488.

Implantable ports suitable for use in the systems of the present invention are described in U.S. patent application Ser. No. 08/942,990, filed on Oct. 2, 1997, and published PCT Application No. WO 98/31416, the full disclosures of which are incorporated herein by reference.

SUMMARY OF THE INVENTION

The present invention provides improved methods, systems, and kits for removing endogenous fluids from fluid retention sites in a patient. The methods rely on percutaneously introducing an access tube, such as a needle or other tissue-penetrable cannula, to an implanted port connected to the site of endogenous fluid retention. Usually, the port will be internally valved so that it is normally closed when the access tube is not present. Introduction of the access tube opens the port and permits removal of at least a portion of the endogenous fluid from the site through a fluid conductive path defined by the access tube and the port. While the present invention is useful for the removal of virtually any endogenous fluid from any patient tissue site where such fluids may collect and be retained, the present invention is not intended to be used with circulating fluids, such as blood, but rather with non-circulating endogenous fluids, such as pleural fluids or effusions which can collect in the pleural cavity as a result of inflammation of the pleura, urine which can collect in the bladder or upper urinary tract as a result of intentional or unintended blockage of the urethra or ureter, cerebrospinal fluid (CSF) which can collect in the meninges in hydrocephalus patients, ascites which can collect in the abdominal cavity of patients suffering from a variety of conditions, lymph fluid that can collect in the lymph spaces, and the like. The present invention is particularly intended to remove fluids where the accumulation is associated with diseased or abnormal conditions and further where it is desired to remove at least a major portion of the fluid which has collected, typically at least 50 percent by volume, preferably at least 75 percent by volume, and more preferably at least 90 percent by volume, or higher.

The present invention relies on forming a fluid conductive path from the fluid retention site in the body, such as the bladder, pleural cavity, upper urinary tract, meninges, abdominal cavity, or the like, to the implanted port, and periodically through the access tube which is selectively percutaneously introduced to the implanted port. The manner in which the implanted port is fluidly connected to the target site is not critical. In some instances, it may be possible to directly connect a fitting, aperture, or other entry point on the port to the target site. More usually, however, connection will be achieved using an implanted drainage cannula, such as a flexible tubular cannula between the target site and the implanted port. A proximal end of the access tube, in turn, will usually be connected to a fluid collection receptacle which may be a simple fluid collection bag, bottle, or other collection device, e.g., drained directly into open waste container under gravity drainage. In some instances, it may be desirable to provide an "active" collection system which is capable of applying a vacuum directly to the access tube or a catheter connected to the access tube in order to draw fluid from the retention site. The vacuum may be supplied by a syringe, pump, or other conventional vacuum-applying system.

The present invention further provides methods for implanting an endogenous fluid removal system in a patient. A drainage cannula is implanted so that a distal end thereof is positioned at a site of endogenous fluid collection. A port connected to a proximal end of the drainage cannula is implanted at a site remote from the site of endogenous fluid collection. After healing, both the drainage cannula and the port are located subcutaneously so that many of the disadvantages of transcutaneous fluid collection systems are avoided.

Subsequent access to the implanted port using an access tube may be achieved by the access methods described above. Usually, introduction of the access tube into the port opens a normally closed internal valve to permit fluid flow from the retention site to the access tube through the implanted drainage cannula and port. Preferred drainage sites in which the drainage cannula is implanted include the bladder, the pleural cavity, and the like.

Systems according to the present invention for removing endogenous fluids from a patient comprise an implantable cannula and an implantable port. The implantable cannula has a distal end adapted for implantation at a site of endogenous fluid retention is patient, such as the bladder, pleural cavity, or the like. By "adapted for implantation," it is meant that the distal end of the implantable drainage cannula will have dimensions, geometries, material properties, and other aspects which are particularly intended for long-term or permanent implantation at the fluid retention site. Specific designs are described hereinafter. The implantable port will preferably include a normally closed internal valve, as described above, and will be accessible via percutaneous introduction of an access tube, also as described above. The systems may optionally include as aspirator comprising the access tube and further comprising a vacuum device capable of drawing a vacuum on the access tube, such as a syringe, vacuum pump, or the like.

The present invention still further comprises aspirators for use in combination with an implantable port to draw fluids therethrough. The aspirator comprises an access tube having a distal end adapted to percutaneously connect to an implanted port. A vacuum device connectable to the access tube is provided to draw fluids from an implanted port through the access tube. The device will still further include a receptacle for collecting fluids from the access tube as they are withdrawn by the vacuum device. In the exemplary embodiment, the vacuum device is a syringe. Pumps and other continuously powered vacuum devices may also be used.

The present invention additionally provides kits intended to facilitate practice of the methods of the present invention. In a first instance, a kit for removing endogenous fluids from a patient comprises an access tube adapted for percutaneous introduction to an implanted port. Often, the kit may comprise a collection bag or other receptacle, a syringe or other vacuum device, connecting tubing, and other components useful in practicing the methods of the present invention. The kit will further comprise instructions for use setting forth a method for removing endogenous fluids from a patient in accordance with any of the methods described above. Optionally, the kit will further comprise packaging materials, usually comprising packaging materials which maintain the access tube in a sterile condition.

In a second aspect, a kit for implanting an endogenous fluid removal system in a patient comprises a drainage cannula, a port, and instructions for use setting forth a method for implanting the cannula in the port in accordance with any of the methods of the present invention. The kit may also comprise packaging, usually for maintaining the kit components in a sterile condition.

DESCRIPTION OF THE SPECIFIC EMBODIMENTS

Figure 1:
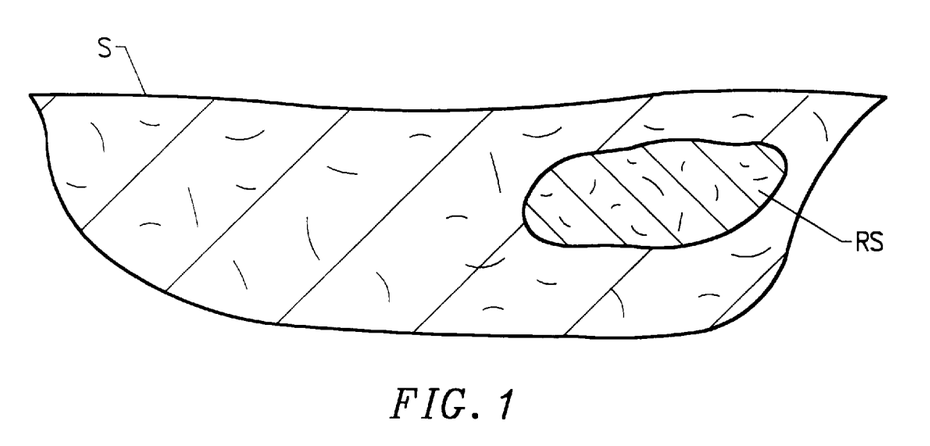
FIGS. 1–5 illustrate a method according to the present invention for implanting a drainage cannula and access port to a subcutaneous site of fluid collection in a patient.
Figure 2:
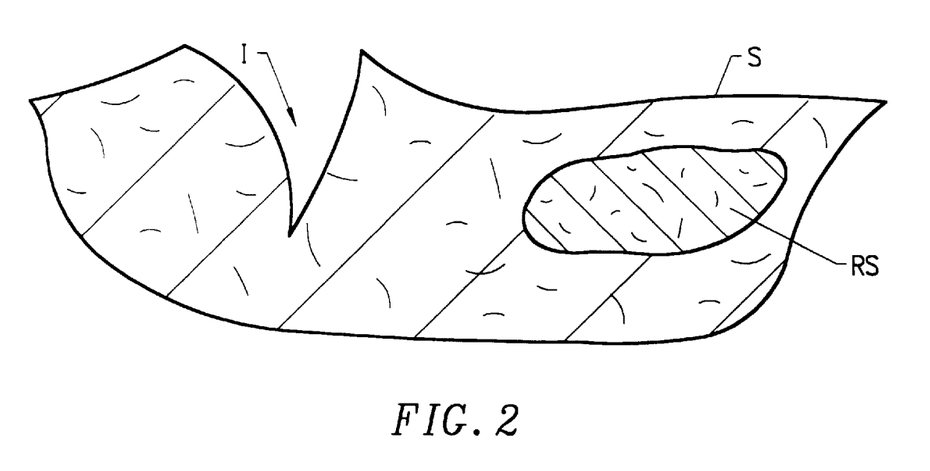
Figure 3:
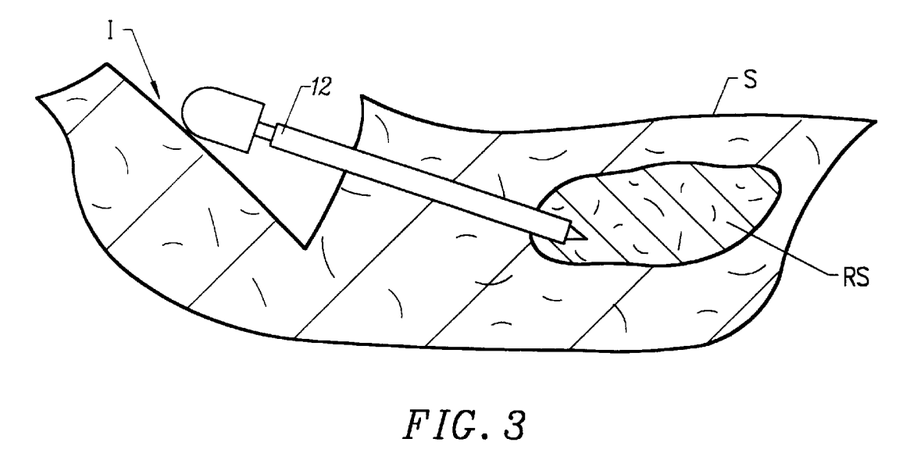
Figure 4:
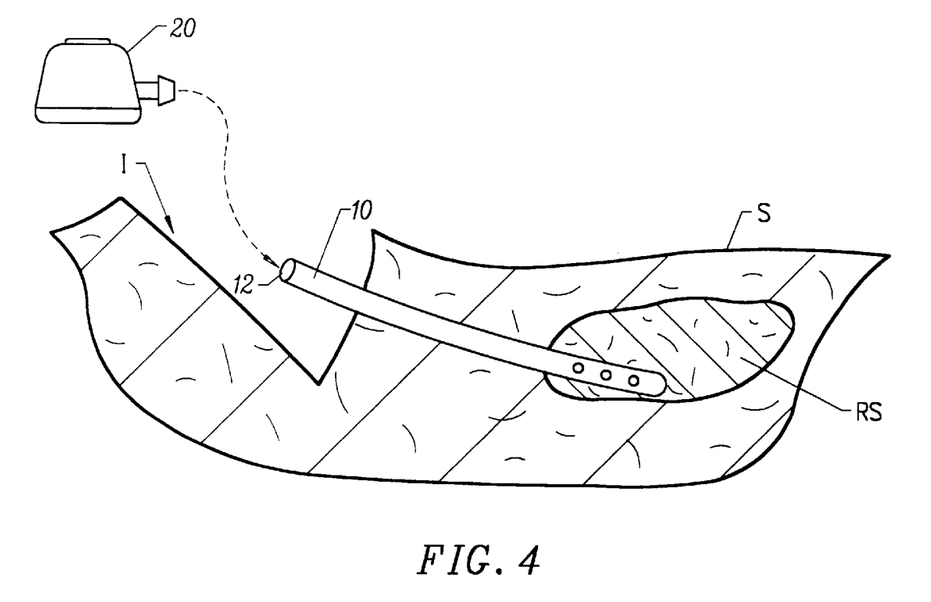
Figure 5:
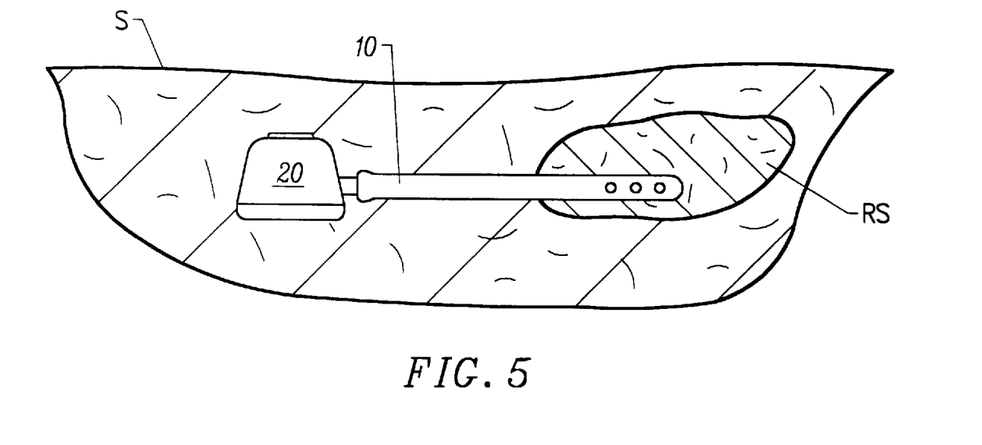

According to the present invention, methods, systems, apparatus, and kits are provided for removing endogenous fluids, as defined above, from a variety of subcutaneous retention sites in a human or animal body. Exemplary fluid retention sites are listed above and illustrated schematically in FIG. 1, where a retention site RS is shown beneath a patient's skin S. Regardless of the actual retention site, methods for implanting a drainage cannula and access port may be generally similar and are illustrated in FIGS. 2–5. An incision I may be made through the skin and into underlying tissue at a location remote from the retention site RS, as shown in FIG. 2. The depth of the incision, location, distance from the retention site RS, and the like, may vary depending on the particular retention site and individual patient. In most instances, however, the depth of incision, corresponding to the depth of implantation of the bottom of the port, will generally be from 1 cm to 5 cm and the distance of the implantation site from the retention site will generally be in the range from 1 cm to 50 cm. After forming the incision I, a preferred method for implanting a drainage catheter 10 (FIG. 4) is to first create a subcutaneous access tract, e.g., using a penetrating tool 12, as shown in FIG. 3. The penetrating tool can be a simple stylet, but could also be a combination stylet/cannula, radially-expansible cannula, or other conventional tunneling tool. After a subcutaneous access tract is formed, the drainage cannula 10 may be implanted with its distal end within the retention site RS, as illustrated in FIG. 4. A proximal end 12 of the drainage cannula 10 will remain within the incision I and be available for connection to an implantable port 20. Optionally, the proximal end of the drainage cannula 10 may be cut to length prior to connection to the port. In other instances, however, the cannula may be pre-connected to the port, or may even be an integral part of the port. Preferred implantable ports 20 will have internal valves, more preferably having normally closed valves which are opened in response to insertion of an access tube, as described hereinafter. Exemplary ports are described in copending application Ser. No. 08/942,990, the full disclosure of which is incorporated herein by reference. This application has been published as PCT Application No. WO 98/31416. Other suitable implantable ports are described in U.S. Pat. Nos. 5,741,228; 5,702,363; and 5,356,381, the full disclosures of which are incorporated herein by reference. After the drainage cannula 10 and port 20 have been implanted, the incision I is closed in a conventional manner and the surrounding tissue allowed to heal. After a time, the access cannula 10 and port 20 will both be positioned subcutaneously beneath the patient's skin S, as illustrated in FIG. 5.

Figure 6:
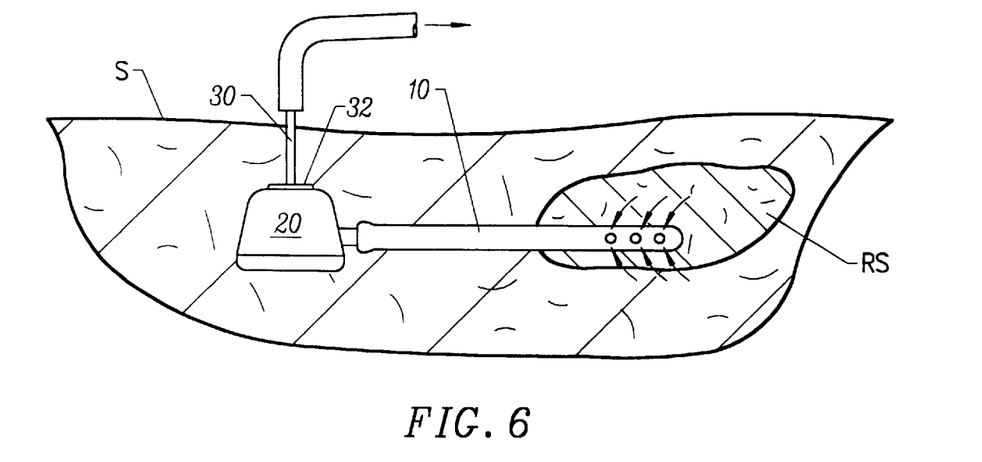
FIG. 6 illustrates a method for withdrawing endogenous fluids through an implanted port and drainage catheter according to the methods of the present invention.

After implantation, the port 20 is available for establishing temporary access using an access tube 30, as illustrated in FIG. 6. The access tube 30, which may be a sharp needle, a blunt needle, a cannula/stylet assembly, or other conventional access conduit, will be introduced percutaneously to an aperture 32, preferably located on a portion of the port lying closest to the surface of the skin S. Insertion of the access tube 30 will preferably open a normally closed valve within the port to establish access from the retention site RS, through the drainage catheter 10, through internal passages within the port 20, and thereafter out through a lumen in the access tube. Retained fluids may thus be withdrawn through the access tube 30, optionally with the application of a vacuum to the tube 30, as discussed hereinafter. Alternatively, for fluids under internal pressure, no vacuum need be applied and the fluids will flow naturally once an access path opening to atmospheric pressure has been established.

Preferred methods and techniques for introducing an access tube 30 to an implanted port 20 are described in copending application Ser. Nos. 08/896,790 and 08/896,592, the full disclosures of which are incorporated herein by reference. Preferably, the access tubes 30 will be percutaneously introduced in a generally vertical direction, i.e., normal to the surface of the skin at the point through which they are introduced. More preferably, the access tubes 30 will be introduced in a manner which creates and relies on the formation of a "button hole," as described in copending application Ser. No. 08/896,592, the full disclosure of which is also incorporated herein by reference. Preferably, the tissue tract through which the access tube 30 is introduced will be disinfected prior to and/or after each accession. Preferred methods for disinfecting the tissue tract and region surrounding the implanted port are described in copending application Ser. No. 09/003,772, the full disclosure of which is incorporated herein by reference. Usually, a disinfectant material, such as an antibiotic or antiseptic material, is injected into the tissue pocket surrounding the implanted port. Excess disinfectant will preferably flush the internal components of the implanted port as well as the tissue pocket surrounding the port and tissue tract leading to the port in order to reduce the risk of infection of the port in surrounding tissue. Usually, the port will remain closed while the disinfectant is being introduced.

Figures 7, 7A:
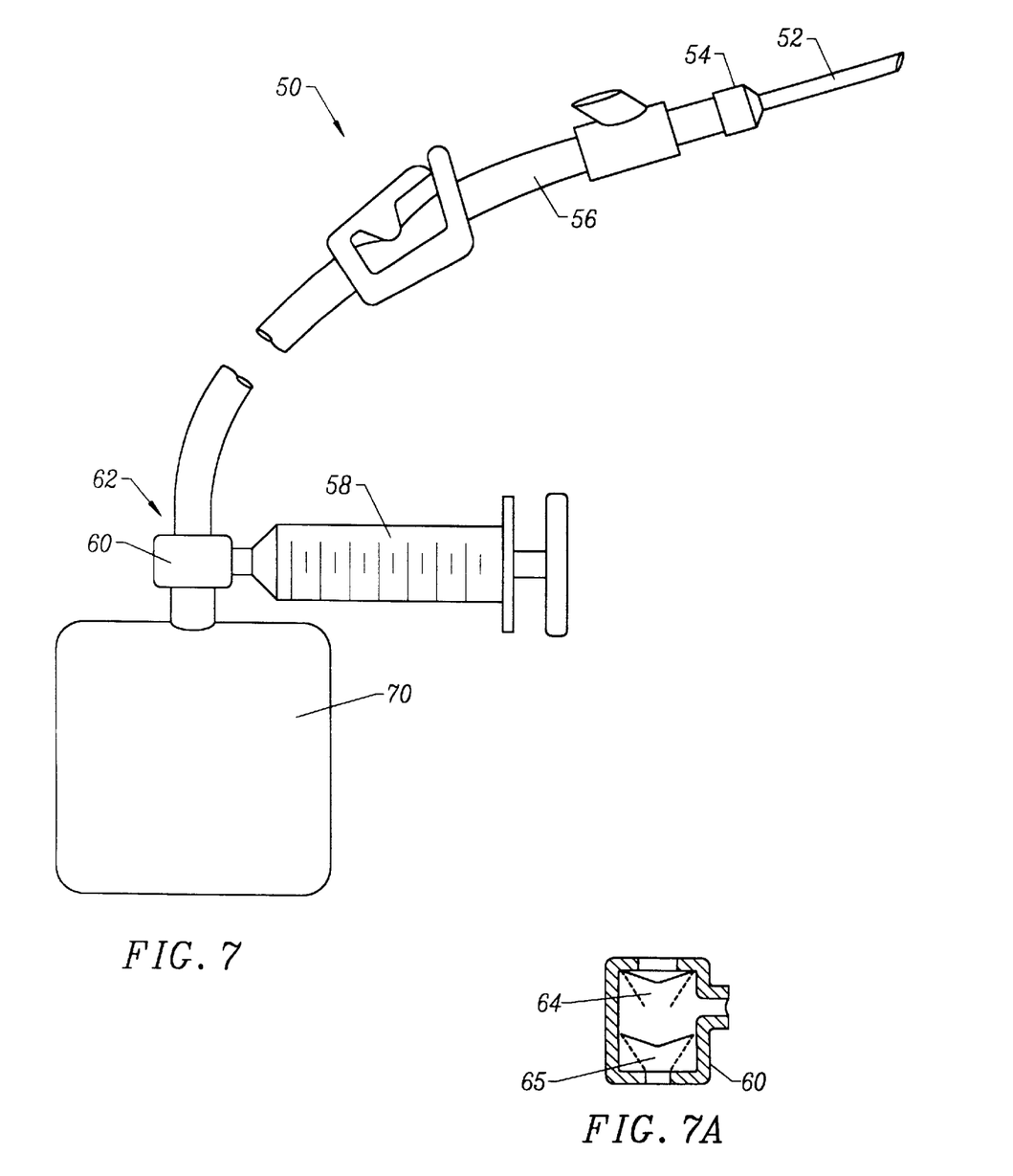
FIGS. 7 and 7A illustrate a vacuum-assisted aspirator for collecting fluids according to the methods and systems of the present invention.

Referring now to FIG. 7, an exemplary aspirator for applying a vacuum to an implanted port to remove body fluids will be described. The aspirator 50 comprises an access tube 52, typically a needle, needle/stylet combination, or the like, capable of direct percutaneous introduction to an implanted port. The needle is connected to a distal end 54 of a catheter 56 or other flexible tube. A syringe 58 is connected to a valve assembly 60 and a proximal end 62 of the catheter 56. Valve assembly 60 (FIG. 7A) comprises a pair of one-way valve elements 64 and 65 which permit the syringe to first draw fluid into its barrel by pulling on the syringe plunger to draw fluid through the one-way valve 64. After filling the barrel, the fluid may be expelled into a collection receptacle 70 by pushing on the plunger to expel the fluid through the one-way valve 65. The aspirator 50 is particularly useful for withdrawing urine from a bladder. Such removal of urine will be useful when the patient's urethra is partially or fully blocked. Such blockage may occur as a result of tumors or other natural causes. Such blockage may also be created intentionally for the treatment of incontinence. In the latter case, urine removal through the implanted port using aspirator 50 or other withdrawal device, will be intended for long-term treatment of the patient.

Figure 8A:
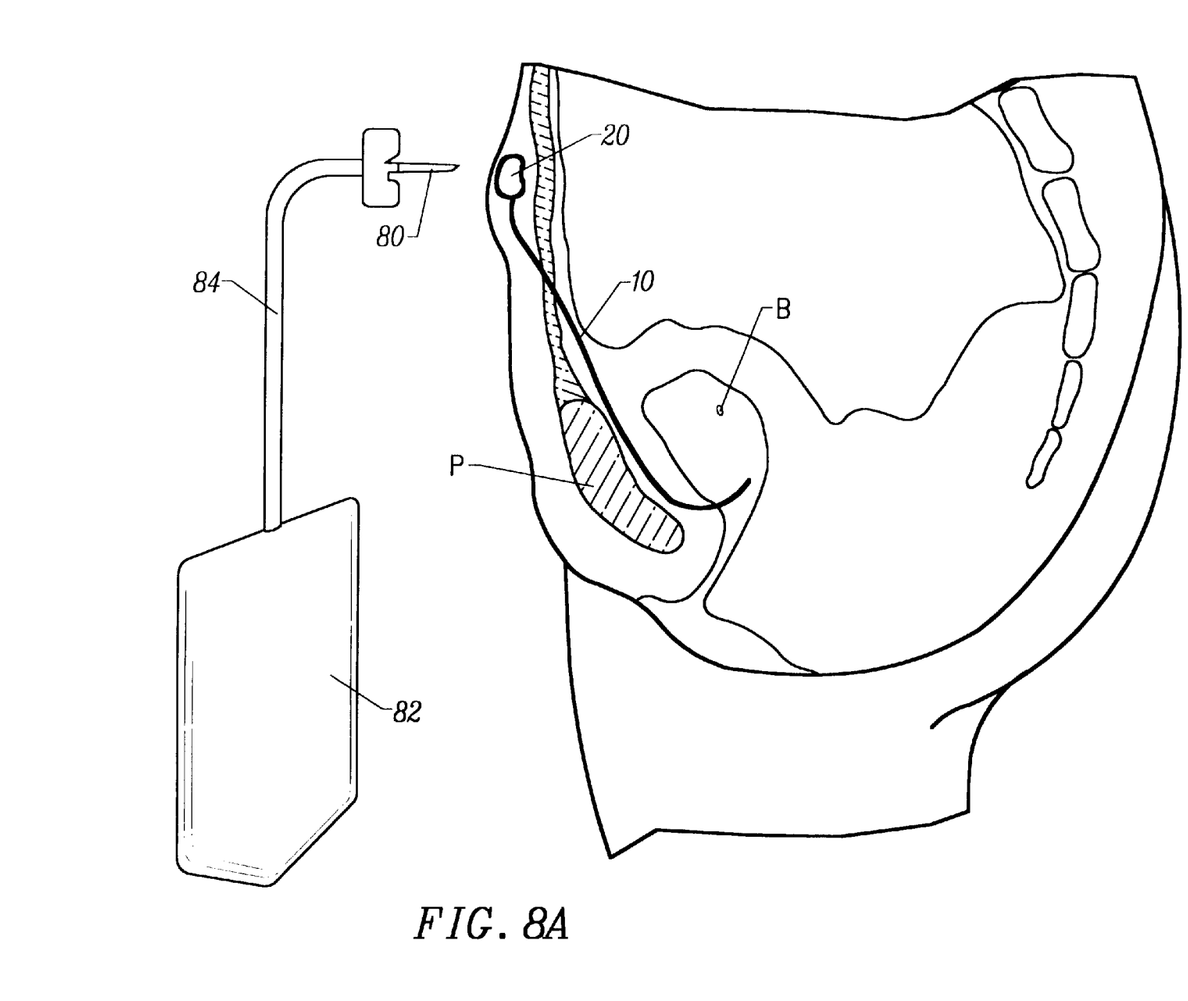
FIGS. 8A and 8B illustrate an exemplary placement of a drainage cannula and access port for removing urine from the bladder.
Figure 8B:
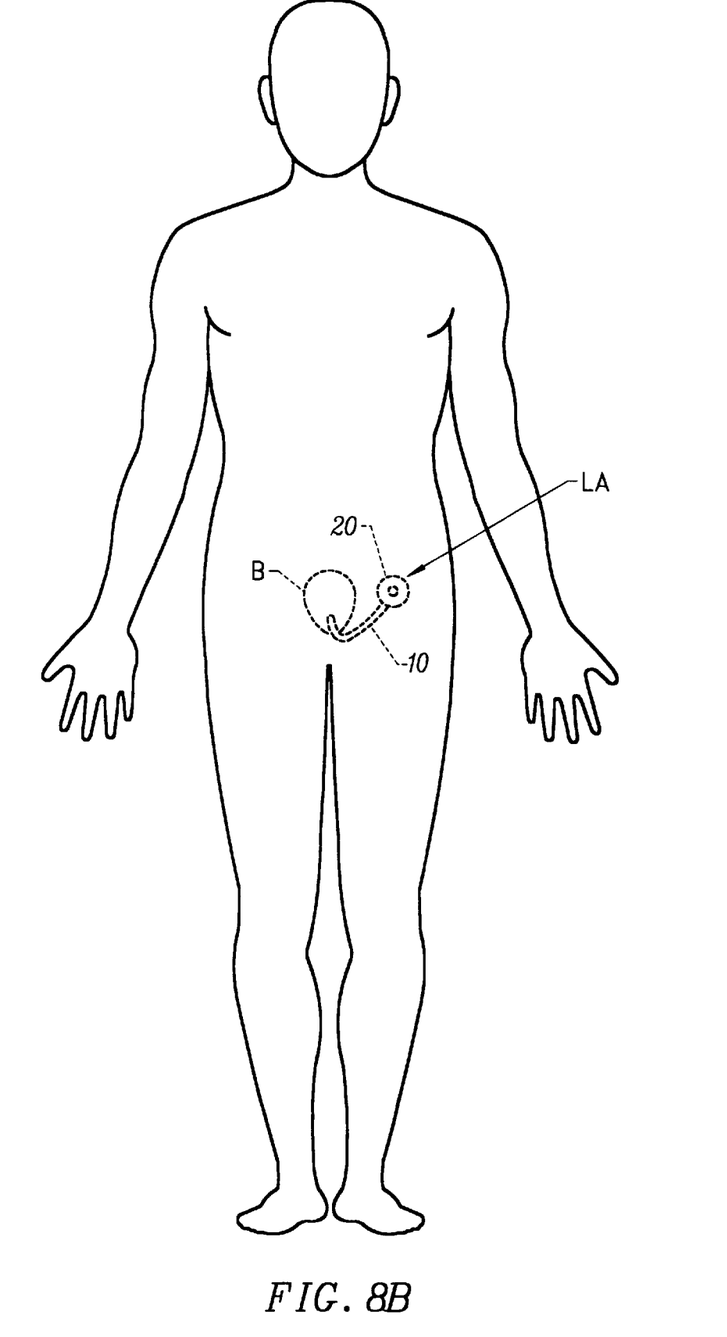

Referring now to FIGS. 8A and 8B, exemplary placement of a drainage cannula 10 and implanted port 20 for the removal of urine from the bladder B is illustrated. The cannula may be placed suprapubically by a mid-line incision through the linea alba into the extra peritoneal space behind the pubic bone P and into the bladder B. The cannula 10 will then be sutured into the bladder wall. The port 20 is preferably located in the region of the left iliac fossa and sutured to the muscle. After positioning the port 20, the cannula is tunneled, trimmed, and connected to the port. Suitable cannulas 10 will have a diameter of about 5 mm (15 F) and a length of about 30 cm. They may be formed from conventional materials, such as silicone elastomer, and will typically include a radiopaque stripe to enhance fluoroscopic observation.

After implantation, the port 20 can be accessed using a percutaneous needle 80 which is optionally connected to a drainage bag 82. Alternatively, the tube 84 connected to the needle 80 could be drained directly into a toilet. Optionally, syringes or other vacuum-applying means could be used to enhance collection of the urine.

Figure 9:
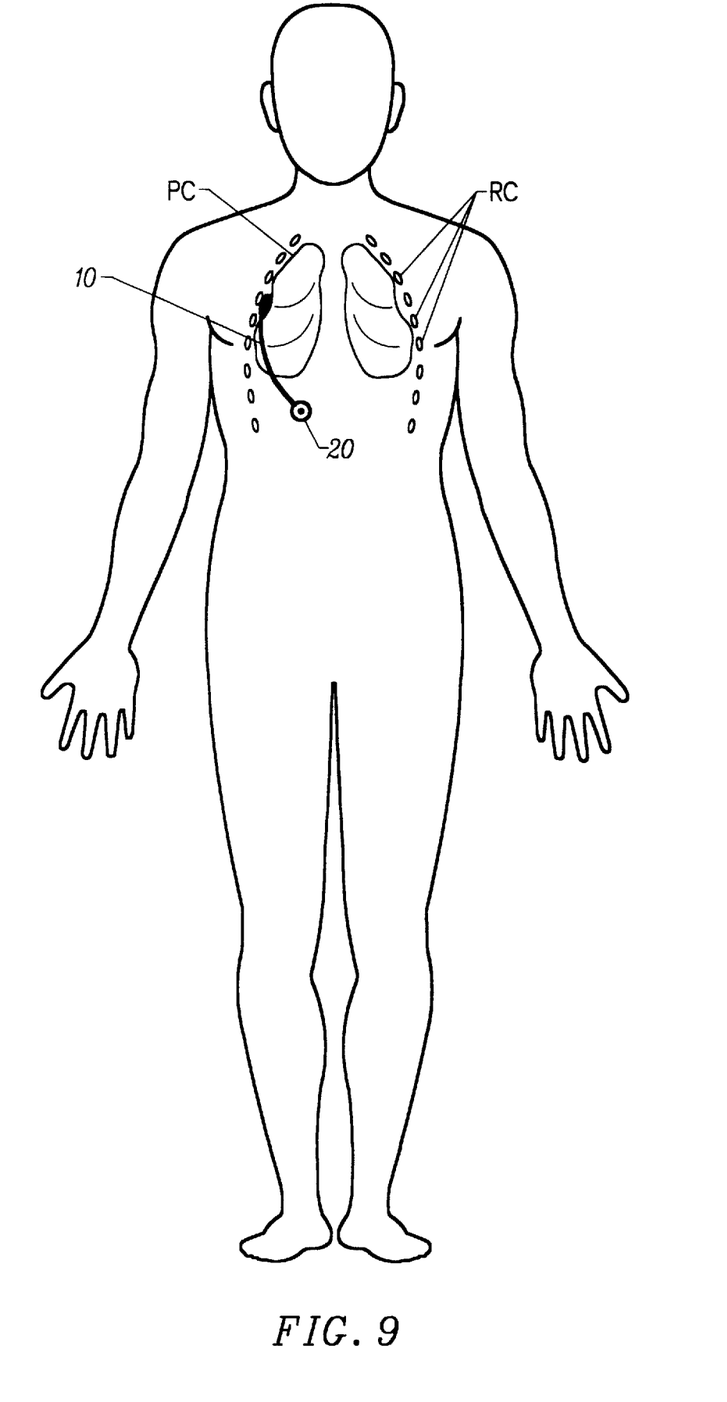
FIG. 9 illustrates an exemplary placement of a drainage cannula and access port for draining fluids from the pleural cavity.

Now referring to FIG. 9, exemplary placement of a drainage cannula 10 and access port 20 for drainage of pleural fluids from a pleural cavity PC is illustrated. The pleural cavity PC is the region overlying the lungs and beneath the rib cage RC. The cannula 10 will usually be run down from a region at which the pleural fluids are collecting to a point, e.g., beneath the rib cage. The cannula 10 may be implanted and connected to the port 20, in a manner analogous to that described above for the bladder connection. The port may then be accessed using an access tube and drained, either by gravity or using a suitable vacuum-applying system.

Figure 10:
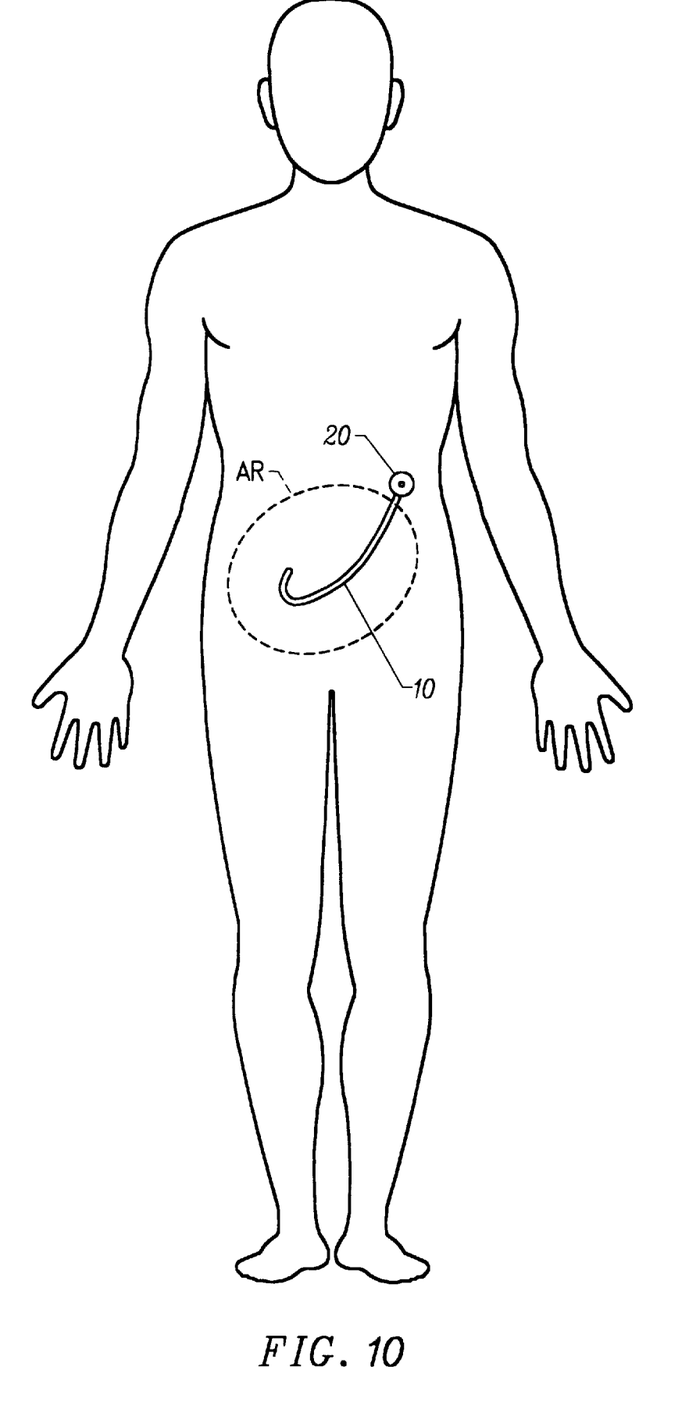
FIG. 10 illustrates an exemplary placement of a drainage cannula and access port for removing ascites fluid from a patient's abdomen.

Referring now to FIG. 10, drainage of ascites which may accumulate in an abdominal region AR of a patient is illustrated in FIG. 10. A cannula 10 is located with its distal, collection end within the region of the abdomen where ascites fluid is collecting. Port 20 is implanted, usually just outside the region where the ascites is collecting. The fluid may be collected through the port, either by gravity or by application of a vacuum, as with the previously described embodiments.

Figure 11:
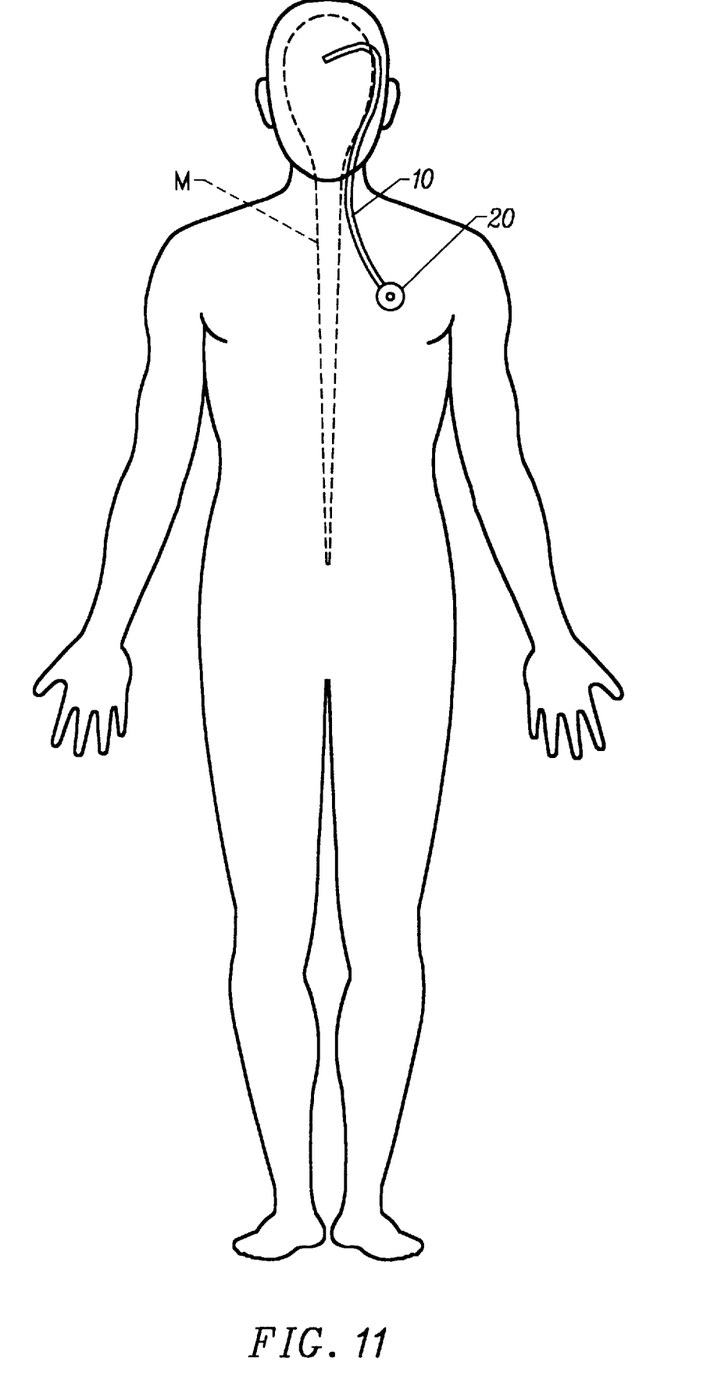
FIG. 11 illustrates an exemplary placement of the drainage cannula and access port for draining cerebrospinal fluid from a patient's meninges.

As a final exemplary embodiment, the cannula 10 and port 20 may be connected to drain cerebrospinal fluid (CSF) from a region within a patient's meninges M, as illustrated in FIG. 11. The meninges is a thin membrane which encases the brain and the vertebral column and includes the subarachnoid space, the ventricles, and the brain interstitial spaces. In patients suffering from hydrocephalus, excess CSF may accumulate within the meninges and must be drained in order to reduce intracranial pressures to a safe level. Drainage is effected by implanting the distal, collection end of the cannula within any convenient region within the meninges, typically within a brain ventricle. The cannula 10 is then passed subcutaneously to a region in the patient's torso, typically in the chest region as shown in FIG. 11. The implanted port 20 may then be accessed using an access tube and CSF drained, either by gravity or by applying a vacuum, as generally described for the previous embodiments.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for removing endogenous fluids from a patient, said method comprising:

percutaneously introducing an access tube to an implanted port connected to a site of endogenous fluid retention, wherein the endogenous fluid has accumulated as a result of an abnormal condition; and removing at least 50% by volume of the endogenous fluid which has accumulated at the site through a fluid conductive path defined by the access tube and the port.

2. A method as in claim 1, wherein removing endogenous fluid comprises applying a vacuum through the access tube.

3. A method as in claim 1, wherein the site is selected from the group consisting of the pleural space, the bladder, the abdomen, and the meninges.

4. A method as in claim 3, wherein the fluid is selected from the group consisting of pleural fluid, urine, ascites, and cerebrospinal fluid.

5. A method as in claim 1, wherein the port is normally closed and opens in response to introduction of the access tube.

6. A method as in claim 1, wherein the access tube is introduced in a direction which is substantially perpendicular to the patient's skin at the point where the tube is introduced.

7. A method as in claim 1, further comprising disinfecting the port prior to or after introducing the access tube.

8. A method as in claim 7, wherein disinfecting comprises percutaneously introducing a disinfectant medium to a location in or around the port while the port remains closed.

9. A kit for removing endogenous fluids from a patient, said kit comprising:

an access tube adapted for percutaneous introduction to an implanted port; and instructions for use setting forth a method for removing endogenous fluids from a patient in accordance with the following steps:

percutaneously introducing an access tube to an implanted port connected to a site of endogenous fluid retention, wherein the endogenous fluid has accumulated as a result of an abnormal condition; and removing at least 50% by volume of the endogenous fluid which has accumulated at the site through a fluid conductive path defined by the access tube and the port.

10. A kit as in claim 9, further comprising an aspirator which includes the access tube.

* * * * *